(12) United States Patent
Manus (10) Patent No.: US 11,062,447 B2
(45) Date of Patent: Jul. 13, 2021

(54) HYPERSURFACE RECONSTRUCTION OF MICROSCOPE VIEW (71) Applicant: Brainlab AG, Munich (DE)

(72) Inventor: Johannes Manus, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/955,549

(22) PCT Filed: Sep. 12, 2019

(86) PCT No.: PCT/EP2019/074353
§ 371 (c)(1),
(2) Date: Jun. 18, 2020

(87) PCT Pub. No.: WO2020/094277
PCT Pub. Date: May 14, 2020

(65) Prior Publication Data
US 2021/0012489 A1 Jan. 14, 2021

Related U.S. Application Data (63) Continuation of application No. PCT/EP2018/080109, filed on Nov. 5, 2018.

(51) Int. Cl.
*G06T 7/00* (2017.01)
*G06T 7/50* (2017.01)
(Continued)

(52) U.S. Cl.
CPC .............. *G06T 7/0012* (2013.01); *G06T 7/50* (2017.01); *G06T 7/60* (2013.01); *G16H 30/20* (2018.01); *G06T 2207/10072* (2013.01)

(58) Field of Classification Search
CPC .......... G06T 7/0012; G06T 7/50; G06T 7/60; G06T 2207/10072; G16H 30/20
See application file for complete search history.

(56) References Cited

U.S. PATENT DOCUMENTS

2014/0104270 A1    4/2014  Schlei
2015/0262412 A1*   9/2015  Gruber .................. G06T 19/006
                                                          345/426
2017/0366773 A1   12/2017  Kiraly et al.

FOREIGN PATENT DOCUMENTS

WO     2020094277    5/2020

OTHER PUBLICATIONS

Lee et al. "Multi-modal Imaging, Model-based Tracking, and Mixed Reality Visualisation for Orthopaedic Surgery." Healthcare Technology Letters, vol. 4, issue 5, Nov. 16, 2017, pp. 168-173 (Year: 2017).*

(Continued)

*Primary Examiner* — Jon Chang
(74) *Attorney, Agent, or Firm* — Middleton Reutlinger (57) ABSTRACT

Disclosed is a computer-implemented method of determining a hypersurface image from a tomographic image data set describing a tomographic image of an anatomical body part. The method encompasses a locally depth-of-view-corrected reconstruction of a volumetric data set (pre-operative image data, like CT or MRI image data), in order to e.g. augment volumetric image data onto e.g. a microscope view, or in the head-up display of the microscope. For the depth correction, a surface model of the actual anatomical surface of the anatomical body part is used which encompasses a hypersurface reconstruction pf the volumetric data set. Thus, the correct information related to the tissue at the current visible surface is overlaid.

15 Claims, 3 Drawing Sheets (51) Int. Cl.
  G06T 7/60    (2017.01)
  G16H 30/20   (2018.01)

(56) References Cited

OTHER PUBLICATIONS

Jenkins et al. "Using Handheld Stereo Depth Camera to Overcome Limited Field-of-View in Simulation Imaging for Radiation Therapy Treatment Planning." Medical Physics, 44(f), May 2017, pp. 1857-1864 (Year: 2017).*

Potter et al. "Cost-Effective Surgical Registration Using Consumer Depth Cameras." SPIE vol. 9786, 97861W, 2016, 13 pages (Year: 2016).*

International Search Report and Written Opinion for Application No. PCT/EP2019/074353 dated Nov. 27, 2019.

Perrine et al. "Augmented virtuality based on stereoscopic reconstruction in multimodal image-guided neurosurgery: methods and performance evaluation." HAL Id: inserm-00136469; http://www.hal.inserm.fr/inserm-00136469 dated May 16, 2007. 13 Pages.

Seitel et al. "Towards markerless navigation for percutaneous needle insertions", International Journal of Computer Assisted Radiology and Surgery, Springer, DE, vol. 11, No. 1, May 28, 2015. pp. 107-117, XPO35766545, ISSN: 1861-6410, DOI: 10.1007/S11548-15-1156-7.

Kilgus et al. "Mobile markerless augmented reality and its application in forensic medicine", International Journal of Computer Assisted Radiology and Surgery, Springer, DE, vol. 10, No. 5, Aug. 23, 2014. pp. 573-586, XP035492367, ISSN: 1861-6410, DOI: 10.1007/S11548-014-1106-9.

Petersch et al. "3D Soft Segmentation and Visualization of Medical Data Based on Nonlinear Diffusion and Distance Functions", EUROVI06; Joint Eurographics—IEEE VGTC Symposium on Visualization, Jan. 1, 2006, pp. 331-338, XP055020455, Lisbon, Portugal DOI: 10.2312/VisSym/EuroVis06/331-338 ISBN: 978-3-90-567331-9.

* cited by examiner

Fig. 3

HYPERSURFACE RECONSTRUCTION OF MICROSCOPE VIEW

FIELD OF THE INVENTION

The present invention relates to a computer-implemented method of determining a hypersurface image from a tomographic image data set describing a tomographic image of an anatomical body part, a corresponding computer program, a program storage medium storing such a program and a computer for executing the program, as well as a medical system comprising an electronic data storage device and the aforementioned computer.

TECHNICAL BACKGROUND

Current implementations do a planar oblique reconstruction of the volumetric image data, e.g. at the focal plane of the microscope view. As typically only parts of the visible anatomical surface are in that focal plane and other parts are in front of or behind the focal plane, the incorrect volumetric image data is displayed. Overlaying of image data on the microscope view has so far assumed a planar surface, which is typically only partially true. Therefore, this assumption may lead to erroneous overlaying of image data.

The present invention has the object of providing a data processing method which allows improved overlaying of image data on a view (such as a microscope view) of an anatomical body part.

The present invention can be used for image guided procedures e.g. in connection with a system for cranial navigation with microscope or augmented reality integration such as Kick® or Curve®, both products of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Invention

In the following, a short description of the specific features of the present invention is given which shall not be understood to limit the invention only to the features or a combination of the features described in this section.

The disclosed method encompasses a locally depth-of-view-corrected reconstruction of a volumetric data set (pre-operative image data, like CT or MRI image data), in order to e.g. augment volumetric image data onto e.g. a microscope view, or in the head-up display of the microscope. For the depth correction, a surface model of the actual anatomical surface of the anatomical body part is used which encompasses a hypersurface reconstruction of the volumetric data set. Thus, the correct information related to the tissue at the current visible surface is overlaid.

General Description of the Invention

In this section, a description of the general features of the present invention is given for example by referring to possible embodiments of the invention.

In general, the invention reaches the aforementioned object by providing, in a first aspect, a computer-implemented medical method of determining a hypersurface image from a tomographic image data set describing a tomographic image of an anatomical body part. The method comprises executing, on at least one processor of at least one computer (for example at least one computer being part of a navigation system), the following exemplary steps which are executed by the at least one processor.

In a (for example first) exemplary step, patient image data is acquired which describes a tomographic (i.e. three-dimensional) medical image (i.e. a three-dimensional set of medical image data) of the anatomical body part. The tomographic imaging modality used to generate the patient image data may be any tomographic imaging modality such as a nuclear magnetic resonance-based or x-ray-based tomographic imaging modality. The anatomical body part may be any body part of a patient and for example is at least a part of the head such as the brain or the skull, or in another example an external surface of the patient's body such as the epidermis.

In a (for example second) exemplary step, surface detecting device position data is acquired which describes a relative position between a surface detecting device and the anatomical body part. For example, the relative position is defined between the surface detecting device and an internal or external surface of the anatomical body part. For example, the surface detecting device is a surface scanning device or a medical imaging device such as a microscope or a range camera. The microscope is for example a digital microscope. In one specific example, the microscope is a (for example digital) stereoscopic microscope. In one example of this step, the surface detecting device position data is acquired by determining, using for example a navigation system, surface detecting device marker data describing the position of a marker device attached to the surface detecting device in a predetermined (e.g. at least one of fixed or known) position. Additionally, the surface detecting device position data is acquired for example by determining, using for example a navigation system, patient marker data describing the position of a marker device attached to the patient in a predetermined (e.g. at least one of fixed or known) position. Alternatively or additionally, the surface detecting device position data is acquired based on for example a detection characteristic of the surface detecting device. In an example, the detection characteristic is an imaging characteristic such as the focus of the surface detecting device, e.g. the focus value at which the below-mentioned electronic signal is generated. In a further example, the surface detecting device is self-localizing so that it is configured to acquire the surface detecting device position data based on the image data acquired by the surface detecting device which in on specific example includes the patient image data. Further alternatively or additionally, the surface detecting device is attached to a mechanical articulable arm (also called robotic arm) having at least one sensor for outputting signals describing the geometric configuration of the arm. The surface detecting device position data is then acquired based on for example the signals (i.e. at least one signal) output by the sensor.

In a (for example third) exemplary step, depth map data is determined based on at least one electronic signal generated by the surface detecting device, wherein the depth map data describes a surface profile of the surface of the anatomical body part. The surface profile is for example a height (also called depth) profile of the surface.

In a (for example fourth) exemplary step, hypersurface image data is determined based on the patient image data and the surface detection device position data and the depth map data, wherein the hypersurface image data describes a hypersurface image generated from the patient image data. The hypersurface image data is determined for example by doing a hypersurface reconstruction of the patient image data.

In an example of the method according to the first aspect, image display data is determined for displaying the hypersurface image on a display device, wherein the image display data is determined based on the hypersurface image data. The display device is for example at least one of a standard monitor, a head-up display, an augmented reality display device, a virtual reality display device, an augmented virtual reality display device, a mixed reality display device, or a microscope. Accordingly, the display is for example executed by displaying the image display data (specifically, the hypersurface image) as augmentation information. In one specific example, the hypersurface image is displayed by injecting it in the microscope, i.e. overlaying it on an image of the anatomical body part generated by the microscope.

In an example of the method according to the first aspect, surface projection data is determined based on the patient image data and the surface detecting device position data and the surface data, wherein the surface projection data describes a positional transformation between the position of the surface profile of the surface of the anatomical body part and a corresponding position (within the framework of this disclosure also called transformed position) in the tomographic medical image. The positional transformation constitutes a mapping between an in situ surface image (shown e.g. in the microscope image) and the patient image data. The hypersurface image data is then determined for example further based on the surface projection data. Specifically, the rendering of the hypersurface image data is determined based on the surface projection data because the viewing angle onto the hypersurface determines the rendering.

In an example of the method according to the first aspect, the positional transformation is applied to the position of the surface profile of the surface of the anatomical body part. Thereby, the transformed position of the surface profile is determined. The hypersurface image data is then determined for example by interpolating, at the transformed position, at least one image intensity value of the tomographic medical image. This may be done using for example a tri-linear or tri-cubic interpolation algorithm or an interpolation algorithm of higher order. For example, positional information defining the tomographic medical image is defined on a positional grid and wherein the at least one image intensity value is interpolated at a position defined in the positional grid (for example to lie on a node or between nodes of the grid) by considering at least one intensity value (for example, a plurality of intensity values) described by a neighbourhood of positions on the positional grid around the transformed position.

In an example of the method according to the first aspect, surface image data is acquired, from the at least one electronic signal, which describes a surface image of the anatomical body part (e.g. a two-dimensional medical image of the anatomical body part). The surface image data is for example digital image data describing the surface scanner or camera or microscope image, depending on the type of surface detecting device use. The depth map data is the determined for example based on the surface data.

In an example of the method according to the first aspect, surface detecting device calibration data is acquired which describes an extrinsic or intrinsic calibration of the surface detecting device. If the surface (e.g. the two-dimensional medical image) is then generated for example from two stereoscopic datasets (e.g. sub-images, only one of the stereoscopic datasets being assigned to each one of the imaging units of a stereoscopic imaging device such as a stereoscopic microscope or a stereoscopic surface scanner) acquired with the surface detecting device, the depth map data is determined for example based on the surface detecting device calibration data and by determining, in the two stereoscopic datasets, corresponding surface regions (e.g. corresponding image regions). The corresponding surface regions and the geometric profile are determined by applying an image fusion algorithm (for example, an elastic image fusion algorithm) to the stereoscopic datasets. Alternatively, the corresponding surface regions are determined for example by conducting a pixel-wise comparison of the contents of the stereoscopic datasets and the surface profile is then determined for example based on the result of the comparison and by applying a triangulation algorithm (as known for example from parallax computation). Further alternatively, the surface profile may be extracted directly from the electronic signal, for example in the case of the surface detecting device being a range camera.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  a) the at least one computer according to the fourth aspect;
  b) at least one electronic data storage device storing at least the patient image data;
  c) the surface detecting device for generating the electronic signal for determining the depth map data; and
  d) a display device for displaying the hypersurface image data,
    wherein the at least one computer is operably coupled to the at least one electronic data storage device for acquiring, from the at least one data storage device, at least the patient image data, the surface detecting device for acquiring, from the surface detecting device, at least the surface data, and the display device for sending, to the display device, at least one signal to cause the display device to display the hypersurface image data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of performing surgery on the anatomical body part, for example so as to render it visible to the surface detecting device. More particularly, the invention does not involve or in particular comprise or encompass any surgical or therapeutic activity. The invention is instead directed as applicable to processing data. For this reason alone, no surgical or therapeutic activity and in particular no surgical or therapeutic step is necessitated or implied by carrying out the invention.

The present invention also relates to the use of the system according to the fifth aspect for conducting a medical procedure, wherein the use comprises execution of the steps of the method according to any one of the preceding method claims for determining the hypersurface image.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (for example, in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
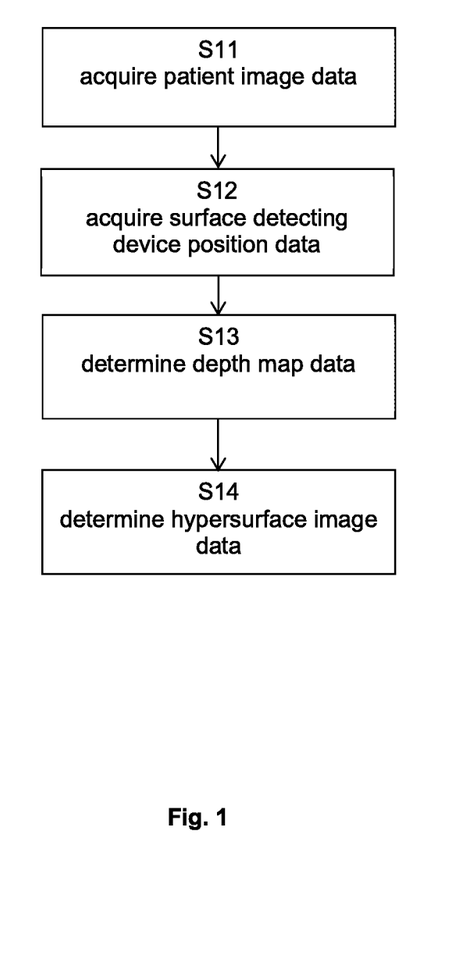
FIG. 1 illustrates the basic steps of the method according to the first aspect.

FIG. 1 illustrates the basic steps of the method according to the first aspect, in which step S11 encompasses acquisition of the patient image data, step S12 encompasses acquisition of the surface detecting device position data and subsequent step S13 encompasses determination of the depth map data. Step S14 is directed to determining the hypersurface image data.

An exemplary workflow comprises the following steps:
1. Load patient image data (e.g. CT).
2. a) Acquire depth map data—for example, from the z-component of RGB-D information.
   b) Acquire depth map-generating device position data.
3. Generate hyper surface from patient image data and depth map data.
4. The pixel positions are given e.g. by the view or projection parameters and the measured depth, in a coordinate system orthogonal to the view direction this gives ($x_i$, $y_i$, depth) for pixel position i. For these positions, the intensity values are calculated by e.g. a trilinear interpolation on the three-dimensional regular grid of the volumetric data set (see also https://en.wikipedia.org/wiki/CT_scan#Multiplanar_reconstruction).
   a. Display as either z-corrected orthogonal view or perspective three-dimensional view on an external monitor or inside the microscope (transparent overlay or in an alternative view).
5. Optional: Update view if depth map changes.

Figure 2:
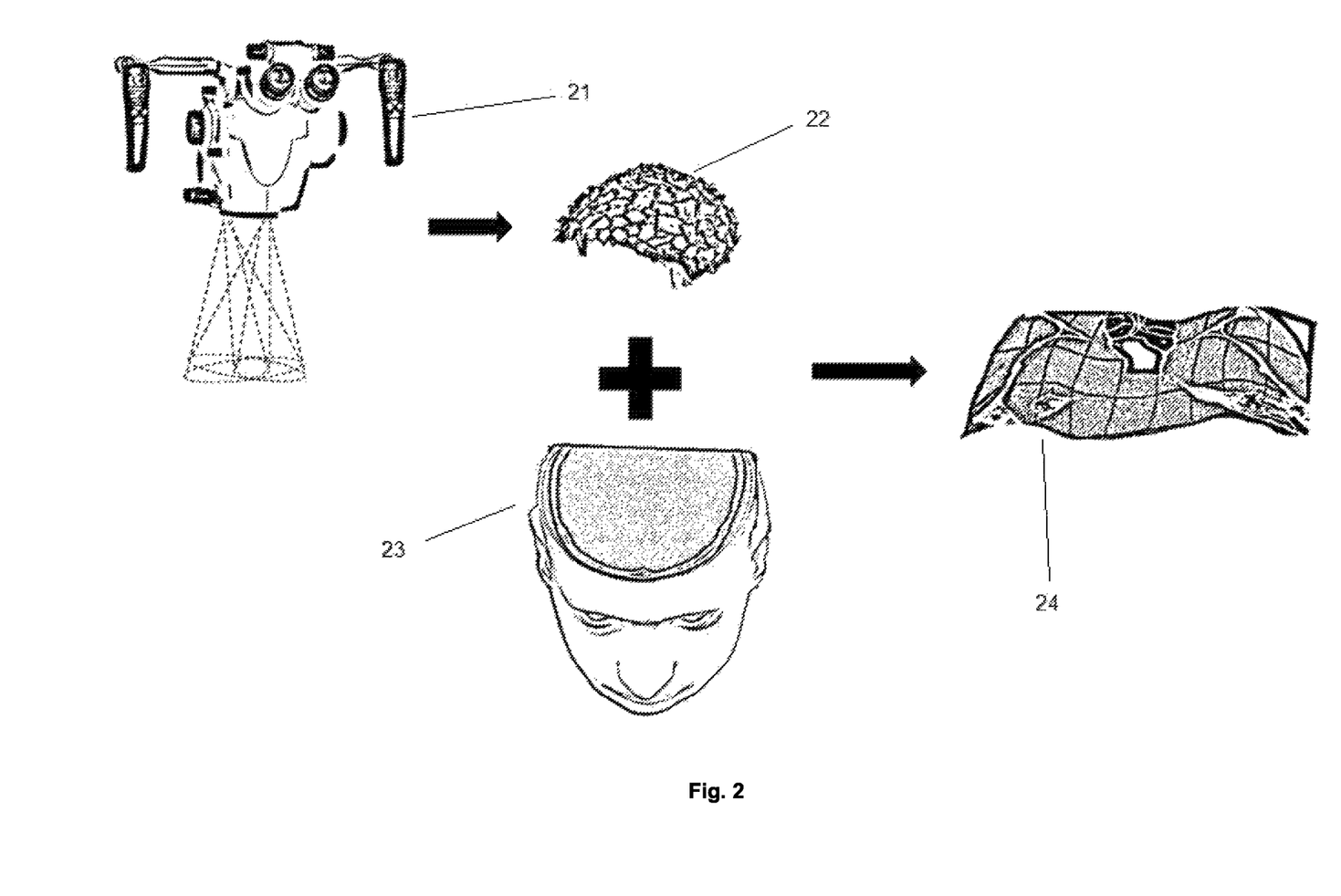
FIG. 2 shows using the stereoscopic microscope images for reconstructing a depth map.

FIG. 2 describes how using the stereoscopic microscope images it is possible to reconstruct a depth map (the microscope video textured on the three-dimensional (3D) surface reconstructed from the stereo video). Instead of a video-textured 3D surface, a hyper-surface reconstruction (HSR) of a patient data set (e.g. MRI or CT) is performed and augmented on the microscope video or used for other display modes like the microscope depth view or for replacing the microscope depth view by the HSR view. Hypersurface reconstruction means—instead of doing a multiplanar reconstruction (MPR) through e.g. the focal plane of the microscope 21—doing a reconstruction (intersection) of the curved free-form surface 24 (hyper-surface) generated by the depth map 22 (surface profile) with the patient image data. The Mercator view is an example for a hyper-surface reconstruction:

The conventional Mercator projection is a projection of a sphere onto a plane and is often used for creating world maps. The following formula defines the conventional Mercator projection in terms of longitude λ and latitude φ, where the x-axis is the projection of the equator and the y-axis is at longitude $\lambda_0$:

$$x = R(\lambda - \lambda_0)$$
$$y = R\ln\left[\tan\left(\frac{\pi}{4} + \frac{\phi}{2}\right)\right]$$

where R is the radius of the spherical surface. The corresponding formulae for spherical coordinates θ and φ are $$x = R(\varphi - \varphi_0)$$
$$y = R\ln\left[\tan\left(\frac{\pi}{2} - \frac{\theta}{2}\right)\right]$$
$$\theta = \frac{\pi}{2} - \phi$$

where φ=λ is the angle to the x-axis measured in the xy-plane, and the angle to the z-axis. The inverse projection is given by:

$$\theta = \pi - 2\tan^{-1}(e^{y/R})$$
$$\varphi = \frac{x}{R} + \varphi_0$$

For use with the present invention, this original Mercator projection is modified such as to optimize the visibility of important regions of the brain which are poorly visible in the original Mercator projection, e.g. the temporal lobes. The latter get stretched a bit in the modified projection, in order to make them occupy a larger region in the projection.

The actual form of the brain 23 is taken into account as follows. The conventional Mercator projection projects a function defined on a spherical surface onto a plane. Since we want to project a (in general non-spherical) surface of a given distance to the cortex surface onto a plane, we need to adapt the Mercator projection to a non-spherical surface. This is achieved by defining the surface of a given distance to the cortex surface by its radius r(θ, φ) as a function of the angular coordinates θ and φ. r(θ, φ) is expanded in real-valued spherical harmonics up to a given order $l_{max}$, e.g. up to order 7:

$$r(\theta, \varphi) = \sum_{l=0}^{l_{max}} \sum_{m=-l}^{l} r_{lm} Y_{lm}(\theta, \varphi)$$

where $r_{lm}$ are real-valued coefficients determined from the surface we want to describe, and the real-valued spherical harmonics are defined as follows:

$$Y_{lm} = \begin{cases} \sqrt{2}\sqrt{\frac{(2l+1)(l-|m|)!}{4\pi(l+|m|)!}} P_l^{|m|}(\cos\theta)\sin(|m|\varphi) & m < 0 \\ \sqrt{\frac{(2l+1)}{4\pi}} P_l^m(\cos\theta) & m = 0 \\ \sqrt{2}\sqrt{\frac{(2l+1)(l-m)!}{4\pi(l+m)!}} P_l^m(\cos\theta)\cos(m\varphi) & m > 0 \end{cases}$$

with $P_l^m$ (cos θ) being the associated Legendre-Polynomials. Note that expansion up to order $l_{max}=0$ results in a spherical surface. The point of the MR or CT image given by r(θ, φ) is then projected with the modified Mercator projection described above for the corresponding point on the corresponding spherical surface.

With that one overlays the structures of the data set which correspond to the part visible in the microscope view for the whole display—independent of the surface lying in, in front of or behind the focal plane.

Of course, it is not restricted to stereo depth maps—any measurement technology for determining a 3D surface/depth information could be used.

Figure 3:
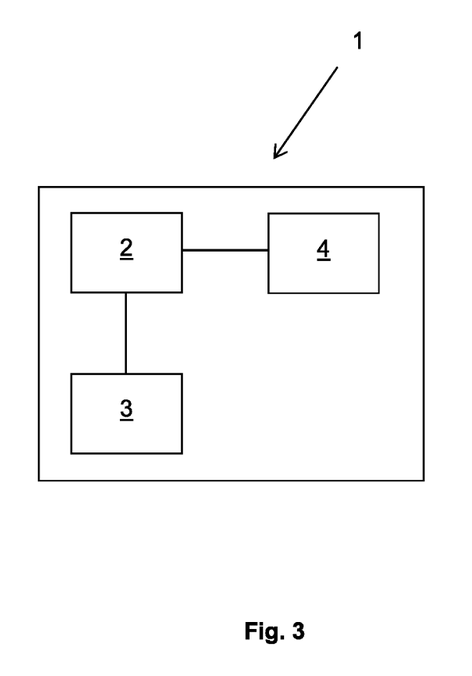
FIG. 3 is a schematic illustration of the system according to the fifth aspect.

Variations of the above-described features of the present invention could be:
Different image modalities for the patient image data:
CT
MR
US
Pre- or intraop. Data Different ways of depth map generation:
 Structure Light scanners
 Time-of-flight cameras
 Depth from focus algorithms
 Stereo imaging
 Range imaging
Different display devices:
 Monitors
 3D monitors
 HUD displays
 AR devices (goggles)
 Microscope injection
Different viewing modalities
 Augmented Reality views
 Virtual reality views
 o Augmented virtuality views
 o Mixed Reality FIG. 3 is a schematic illustration of the medical system 1 according to the fifth aspect. The system is in its entirety identified by reference sign 1 and comprises a computer 2, an electronic data storage device (such as a hard disc) 3 for storing at least the patient data and a medical device 4 (such as a radiation treatment apparatus). The components of the medical system 1 have the functionalities and properties explained above with regard to the fifth aspect of this disclosure.

The present invention provides for two effects:
 Correct corresponding volumetric data is displayed in reconstruction views.
 Correct corresponding augmented reality views are displayed.

The invention claimed is:

1. A computer-implemented medical method of determining a hypersurface image from a tomographic image data set describing a tomographic image of an anatomical body part of a patient, the method comprising the following steps:
 acquiring patient image data which describes a tomographic medical image of the anatomical body part;
 acquiring surface detecting device position data which describes a relative position between a surface detecting device and the anatomical body part;
 determining depth map data based on at least one electronic signal generated by the surface detecting device, wherein the depth map data describes a surface profile of the surface of the anatomical body part;
 determining hypersurface image data based on the patient image data and the surface detecting device position data and the depth map data, wherein the hypersurface image data describes a hypersurface image generated from the patient image data.

2. The method according to claim 1, wherein the surface detecting device is a surface scanning device or a medical imaging device is a microscope or a range camera.

3. The method according to claim 1, further comprising determining image display data for displaying the hypersurface image on a display device, wherein the image display data is determined based on the hypersurface image data.

4. The method according to claim 3, further comprising:
 determining surface projection data based on the patient image data and the surface detecting device position data and the surface projection data, wherein the surface projection data describes a positional transformation between the position of the surface profile of the surface of the anatomical body part and a corresponding position, called a transformed position, in the tomographic medical image,
 wherein the hypersurface image data is determined further based on the surface projection data.

5. The method according to claim 4, wherein
 the positional transformation is applied to the position of the surface profile of the surface of the anatomical body part, thereby determining the transformed position of the surface profile;
 the hypersurface image data is determined by interpolating, at the transformed position, at least one image intensity value of the tomographic medical image.

6. The method according to claim 5, wherein positional information defining the tomographic medical image is defined on a positional grid and wherein the at least one image intensity value is interpolated at a position defined in the positional grid by considering at least one intensity value described by a neighborhood of positions on the positional grid around the transformed position.

7. The method according to claim 1, wherein
 surface image data is acquired, from the at least one electronic signal, which describes a surface image of the anatomical body part, and wherein
 the depth map data is determined based on the surface image data.

8. The method according to claim 1, further comprising:
 acquiring surface detecting device calibration data which describes a calibration of the surface detecting device,
 wherein the surface is generated from two stereoscopic datasets acquired with the surface detecting device, and
 wherein the depth map data is determined based on the surface detecting device calibration data and by determining, in the two stereoscopic datasets, corresponding surface regions.

9. The method according to claim 8, wherein the corresponding surface regions are determined by conducting a pixel-wise comparison of the contents of the two stereoscopic datasets and the surface profile is determined based on the result of the comparison and by applying a triangulation algorithm.

10. The method according to claim 8, wherein the corresponding surface regions and the surface profile are determined by applying an image fusion algorithm to the two stereoscopic datasets.

11. The method according to claim 1, wherein the surface detecting device position data is acquired by determining surface detecting device marker data describing the position of a marker device attached to the surface detecting device in a predetermined position.

12. The method according to claim 11, wherein the surface detecting device position data is acquired by determining patient marker data describing the position of a marker device attached to the patient in a predetermined position.

13. The method according to claim 1, wherein the surface detecting device position data is acquired based on a detection characteristic of the surface detecting device.

14. The method according to claim 13, wherein the surface detecting device is attached to a mechanical articulable arm having at least one sensor for outputting signals describing the geometric configuration of the mechanical articulable arm, and wherein the surface detecting device position data is acquired based on the signals output by the at least one sensor.

15. A medical system, comprising:
 at least one computer executing instructions for determining a hypersurface image from a tomographic image data set describing a tomographic image of an anatomical body part of a patient, the instructions operable to:

acquire patient image data is acquired which describes a tomographic medical image of the anatomical body part;
acquire surface detecting device position data is acquired which describes a relative position between a surface detecting device and the anatomical body part;
determine depth map data is determined based on at least one electronic signal generated by the surface detecting device, wherein the depth map data describes a surface profile of the surface of the anatomical body part;
determine hypersurface image data is determined based on the patient image data and the surface detecting device position data and the depth map data, wherein the hypersurface image data describes a hypersurface image generated from the patient image data;
at least one electronic data storage device storing at least the patient image data;
the surface detecting device for generating the at least one electronic signal for determining the depth map data; and
a display device for displaying the hypersurface image data, wherein the at least one computer is operably coupled to
  the at least one electronic data storage device for acquiring, at least the patient image data,
  the surface detecting device for acquiring, from the surface detecting device, at least the surface data, and
  the display device for sending, to the display device, at least one signal to cause the display device to display the hypersurface image data.

* * * * *